United States Patent
Saleh et al.

(10) Patent No.: US 12,138,103 B1
(45) Date of Patent: Nov. 12, 2024

(54) HETEROGENEOUS BREAST PHANTOM WITH CARCINOMA MODEL

(71) Applicant: Imam Abdulrahman Bin Faisal University, Dammam (SA)

(72) Inventors: Gameel Saleh, Dammam (SA); Budour Alfares, Dammam (SA); AlJohara Aljabr, Dammam (SA); Maryam Zainalabedin, Dammam (SA); Munthreen Almozain, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 18/780,596

(22) Filed: Jul. 23, 2024

Related U.S. Application Data

(63) Continuation of application No. 18/640,409, filed on Apr. 19, 2024, now Pat. No. 12,097,068, which is a
(Continued)

(51) Int. Cl.
*A61B 6/58* (2024.01)
*A61B 6/50* (2024.01)
*A61L 31/00* (2006.01)
(Continued)

(52) U.S. Cl.
CPC ............. *A61B 6/583* (2013.01); *A61B 6/502* (2013.01); *A61L 31/005* (2013.01);
(Continued)

(58) Field of Classification Search
CPC ....... A61B 6/583; A61B 6/502; A61L 31/005; A61L 31/028; A61L 31/042; A61L 31/14; G01R 33/58
See application file for complete search history.

(56) References Cited

U.S. PATENT DOCUMENTS

| | | | |
|---|---|---|---|
| 2014/0180082 A1 | 6/2014 | Evans | |
| 2019/0388054 A1 | 12/2019 | Qiu et al. | |
| 2020/0170612 A1 | 6/2020 | Browne et al. | |

FOREIGN PATENT DOCUMENTS

| | | | | |
|---|---|---|---|---|
| JP | 61210008 A | * | 9/1986 | ............ A61K 8/602 |
| KR | 10-1026833 | | 4/2011 | |
| WO | 2012/040611 A1 | | 3/2012 | |

OTHER PUBLICATIONS

Islam, et al. ; Experimental Breast Phantoms for Estimation of Breast Tumor Using Microwave Imaging Systems ; IEEE Access vol. 6 ; 2018.

Michaelsen, et al. ; Anthropomorphic breast phantoms with physiological water, lipid, and hemoglobin content for near-infrared spectral tomography ; Journal of Biomedical Optics 19(2) ; Feb. 2014.

Franco, et al. ; Manufacturing of physical breast phantoms with 3D printing technology for X-ray breast imaging ; IEEE Nuclear Science Symposium and Medical Imagining Conference ; Nov. 2019 ; Abstract Only.

(Continued)

*Primary Examiner* — Kiho Kim
(74) *Attorney, Agent, or Firm* — Oblon, McClelland, Maier & Neustadt, L.L.P.

(57) ABSTRACT

A heterogeneous patient-based breast phantom that mimics the anatomy and properties of real breast tissues when screened with ionizing and nonionizing imaging modalities is described. The heterogeneous breast phantom includes a skin mimicking segment; an adipose tissue mimicking segment; a fibro-glandular tissue mimicking segment; and a pectoral muscle mimicking segment wherein each segment is shaped and arranged such that the breast phantom represents a breast tissue. Performance of the breast phantom was characterized by mass attenuation coefficient, electron density and effective atomic number. Further, performance of breast phantoms was confirmed CT and breast MRI machines.

8 Claims, 13 Drawing Sheets

Related U.S. Application Data continuation of application No. 17/678,567, filed on Feb. 23, 2022, now Pat. No. 11,998,381.

(51) Int. Cl.
  *A61L 31/02* (2006.01)
  *A61L 31/04* (2006.01)
  *A61L 31/14* (2006.01)
  *G01R 33/58* (2006.01)

(52) U.S. Cl.
  CPC ........... *A61L 31/028* (2013.01); *A61L 31/042* (2013.01); *A61L 31/14* (2013.01); *G01R 33/58* (2013.01)

(56) References Cited

OTHER PUBLICATIONS

Sarno, et al. ; Dataset of patient-derived digital breast phantoms for in silico studies in breast computed tomography, digital breast tomosynthesis, and digital mammography ; Med. Phys. 48 (5) ; May 2021.

Sindi, et al. ; Development of patient-specific 3D-printed breast phantom using silicone and peanut oils for magnetic resonance imaging ; Quant. Imaging Med. Surg 2020.

Ruvio et al., "Multimodal breast phantoms for microwave, ultrasound, mammography, magnetic resonance and computed tomography imaging," Sensors, MDPI, 21 pages. (Year: 2020).

Anwari et al., "3D printed CT-based abdominal structure mannequin for enabling research", 3D Printing in Medicine, vol. 3, No. 3, 12 pages . . . (Year: 2020).

* cited by examiner

HETEROGENEOUS BREAST PHANTOM WITH CARCINOMA MODEL

CROSS-REFERENCE TO RELATED APPLICATIONS

The present application is a Continuation of U.S. application Ser. No. 18/640,409, now allowed, having a filing date of Apr. 19, 2024 which is a Continuation of U.S. application Ser. No. 17/678,567, now U.S. Pat. No. 11,998,381, having a filing date of Feb. 23, 2022.

STATEMENT OF FUNDING ACKNOWLEDGEMENT

This project was funded by the Deanship of Scientific Research, Imam Abdulrahman Bin Faisal University through grant number 2020-053-Eng.

STATEMENT REGARDING PRIOR DISCLOSURE BY THE INVENTORS

Aspects of this technology are described in "Heterogeneous Breast Phantom with Carcinoma for Ionizing Machines" presented at the IEEE IEMTRONICS 2021 conference on Apr. 21, 2021, which is incorporated herein by reference in its entirety.

BACKGROUND

Technical Field

The present disclosure is directed to heterogeneous breast phantoms which can be applied to various breast imaging modalities for the detection of early cancer and lesions. The heterogeneous breast phantom mimics the real breast tissues in terms of anatomy and tissue properties concerning the conventional breast imaging techniques.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The existing medical imaging phantoms have a lot of limitations including unrealistic uniform background structure that does not mimic real organs and tissues. They are mostly designed with homogeneous (of the same properties everywhere in the phantom) solutions for the whole aimed organ with no accurate simulation of tumors, masses or other lesions. Additionally, most of the breast phantoms are tailored to function with a single imaging modality by simulating the tissue material response only for this single modality considering Quality Assurance (QA) only.

Breast cancer is the second most occurring cancer in females and considered as the second reason of mortality as described in Anon., Sep. 14, 2020, https_://www.cdc.gov/cancer/breast/basic_info/index.htm, the entire disclosure is incorporated by reference. Based on the national breast cancer foundation, an estimation of 276 thousand new cases were diagnosed with breast cancer in 2020 and more than 42 thousand women are expected to die in the United States (US) as described by Anon., Nov. 26, 2020, https_://www.nationalbreastcancer.org/wpcontent/uploads/2020-Breast-Cancer-Stats.pdf, the entire disclosure is incorporated herein by reference. However, early stage cancer detection would increase treatment possibilities and the survival rate as described by Anon., Nov. 26, 2020, https_://www.who.int/activities/promoting-cancer-early-diagnosis, the entire disclosure is incorporated herein by reference. Breast phantoms are significant devices that help in early breast cancer detection. They must mimic the properties of the breast tissues with tissue equivalent materials having similar response of the breast when it is screened by each imaging modality. Anthropomorphic breast phantoms are utilized to produce images that simulate aspects of clinical breast screening. They are beneficial in characterization and optimization of breast imaging modalities. In the development of imaging screening technologies, technical assessment for modality optimization through phantoms is essential before the modality can be utilized for clinical use. Nowadays, the existing medical imaging phantoms have a lot of limitations including unrealistic uniform background structure that does not mimic real organs and tissues. They are mostly designed with homogenous solutions for the whole aimed organ with no simulation of tumors, masses, or other lesions.

Phantoms are devices that are being used in the field of medical imaging physics and health science as described by DeWerd and Lawless in "Introduction to Phantoms of Medical and Health Physics," in The Phantoms of Medical and Health Physics: Devices for Research and Development, L. A. DeWerd and M. Kissick, Eds. New York, NY: Springer, 2014, pp. 1-14, the entire disclosure is incorporated herein by reference. They are considered as artificial models that represent the human body to evaluate, examine and tune the performance of several imaging modalities. Phantoms are designed to help in assessing the optimal radiation that is subjected to the patient especially in new emerging imaging techniques and for quality assurance (QA) purposes. Such advanced phantoms that are patient-based can further benefit in hands-on operator training and image-guided interventional procedures. Based on the purpose that the phantom is developed for, the composition and the design process would be established.

In 2015, a group at Duke University developed a breast phantom by matching virtual breast phantoms for mammography projections. The virtual phantoms were made into physical phantoms using additive manufacturing multilateral 3D printing. One design was printed with single additive materials then filled with oil. Second design was made with double additive printed materials for whole breast. The second phantom design offered a better result in term of breast contrast compared to the first design, but the second presented undesirable air bubbles as described by Kiarashi et al. in "Development of realistic physical breast phantoms matched to virtual breast phantoms based on human subject data", Medical Physics, vol. 42, no. 7, pp. 4116-4126, 2015., the entire disclosure is incorporated herein by reference.

Another physical 3D anthropomorphic breast phantom was developed at the University of Pennsylvania for image quality assessment of 2D and 3D breast x-ray imaging systems. The fabricated phantom consists of 45% dense tissue and already 5 cm deformed in thickness for mammography scan. Digital mammographic images with W/Rh at 30 kVp and 104 mAs showed a less than 1% coefficient of variation of the relative attenuation between the two simulated tissues with acceptable appearance with presence of air bubbles as described by Carton et al. in, "Development of a physical 3D anthropomorphic breast phantom," Med.

Phys., vol. 38, no. 2, pp. 891-896, 2011, the entire disclosure is incorporated herein by reference.

Moreover, another method for fabricating breast phantoms was developed by a research group at the Committee for the defense of human right (CDHR). The aim was to model breast X-ray attenuation properties. The phantom was designed only to match full-field digital mammography (FFDM) and digital breast tomosynthesis (DBT). After projections at 35 kVp it was found that both glandular and adipose tissues were acceptable with limitation of masses and lesions insertion to the phantom as described by Rossman et al. in "Three dimensionally-printed anthropomorphic physical phantom for mammography and digital breast tomosynthesis with custom materials, lesions, and uniform quality control region," J. Med. Imaging Bellingham Wash, vol. 6, no. 2, p. 021604, April 2019, the entire disclosure is incorporated herein by reference.

A study was published with an aim to construct breast phantom made from polyethylene by segmenting the patient's breast image into adipose and fibro-glandular tissues. To mimic the different tissues, thermoplastic mold was placed as the outer layer of the skin, fibro-glandular tissue was represented by filling the air gaps with water, while polyethylene and paraffin wax were used to mimic the adipose tissue. Moreover, calcium carbonate particles were used to represent the macrocalcification. The designed phantom model uncompressible breast with an ability to do measurements as described by Prionas et al. in "Development of a Patient-Specific Two-Compartment Anthropomorphic Breast Phantom," Phys. Med. Biol., vol. 57, no. 13, pp. 4293-437 July 2012, the entire disclosure is incorporated herein by reference.

In 2016, a paper published with an aim to develop a multipurpose gel-based breast phantom consisting of a simulated tumor to function with ultrasound, CT, and Magnetic Resonance Imaging (MRI). The Tissue Mimicking Material (TMMs) was ballistic gelatin powder and Metamusil for breast background. Barium sulfate, copper sulfate, water and ballistic gelatin were used for the simulated tumor. The resulted Hounsfield units (HU) of the simulated breast background was 24 HU which was far from the reference value of −100 HU for adipose and 40 HU for fibro-glandular. On MRI, the tumor showed a signal-difference to noise ratio of 3.7 as described by Ruschin et al. in, "Technical Note: Multipurpose CT, ultrasound, and MRI breast phantom for use in radiotherapy and minimally invasive interventions," Med. Phys., vol. 43, no. 5, p. 2508 May 2016, the entire disclosure is incorporated herein by reference.

In 2019, a study was conducted to design a 3D-printed breast phantom for multimodal imaging with TMMs based on a 3D printing. The developed phantom was based on polyvinyl chloride (PVC) including a structure of different lesions, adipose, and fibro-glandular tissues. CT and MRI were used to determine the tissue mimicking properties considering the HU and MRI relaxation times. The results showed that the temperature difference between the PVC softener mixture and the breast mold could present bubbles that affects the image quality and cannot be eliminated. Also, lack of heterogeneity present in the tissues reduces the similarity to the real breast tissues as described by He et al. in "3D-printed breast phantom for multi-purpose and multi-modality imaging," Quant. Imaging Med. Surg., vol. 9, no. 1, pp. 63-74, January 2019, the entire disclosure is incorporated herein by reference.

Recently in 2020, a group at Sapienza University published a phantom for multimodality use. The TMMs were based on different properties such as dielectric properties, acoustic properties, and attenuation coefficient. The phantom used TMMs to simulate the skin, fat tissue, glandular tissue, tumor, and muscle. The phantom resulted in a good match between the reference and the physical measured values with ±10% for the majority of the TMMs. However, the phantom solid parts were compression irreversible because of the fat layer composition. Also, further investigation would be necessary to have more contrast between the tumor and surrounding tissues as described by Ruvio et al. in "Multimodal Breast Phantoms for Microwave, Ultrasound, Mammography, Magnetic Resonance and Computed Tomography Imaging," Sensors, vol. 20, no. 8, Art. no. 8, January 2020, the entire disclosure is incorporated herein by reference.

Despite these recent efforts, there is still a need to develop heterogeneous breast phantoms that effectively mimic real breast tissues.

SUMMARY

In an exemplary embodiment, a heterogeneous breast phantom is described. The heterogeneous breast phantom comprises a skin mimicking segment that comprises polyvinyl alcohol and sugar; an adipose tissue mimicking segment that comprises beeswax; a fibro-glandular tissue mimicking segment that comprises glycerol; and a pectoral muscle mimicking segment that comprises sugar and optionally comprises egg whites, wherein each segment is shaped and arranged such that the breast phantom represents a breast tissue.

In some embodiments, the heterogeneous breast phantom further comprises a carcinoma mimicking segment that comprises sugar.

In some embodiments, each segment further comprises water, a vegetable oil, a surfactant, and agar.

In some embodiments, the vegetable oil is safflower oil.

In some embodiments, the surfactant is a nonionic surfactant.

In some embodiments, the skin mimicking segment, the adipose tissue mimicking segment, the fibro-glandular tissue mimicking segment, and the carcinoma mimicking segment each further comprise at least one type of scattering particles selected from the group consisting of NaCl, KCl, $Al_2O_3$, and SiC particles.

In some embodiments, polyvinyl alcohol and sugar are present in the skin mimicking segment in amounts of 4-6 wt. % and 27-35 wt. %, each relative to a total weight of the skin mimicking segment.

In some embodiments, beeswax is present in the adipose tissue mimicking segment in an amount of 38-45 wt. % relative to a total weight of the adipose tissue mimicking segment.

In some embodiments, glycerol is present in the fibro-glandular tissue mimicking segment in an amount of 10-15 wt. % relative to a total weight of the fibro-glandular tissue mimicking segment.

In some embodiments, sugar is present in the pectoral muscle mimicking segment in an amount of 22-28 wt. % relative to a total weight of the pectoral muscle mimicking segment, and wherein egg whites, if present, are present in an amount of 2-8 wt. % relative to a total weight of the pectoral muscle mimicking segment.

In some embodiments, sugar is present in the carcinoma mimicking segment in an amount of 20-25 wt. % relative to a total weight of the carcinoma mimicking segment.

In some embodiments, the skin mimicking segment has an electron density ($n_e$) of 3.59E+23-3.61E+23 e–/g and an effective atomic number ($Z_{eff}$) of 7.2-7.3.

In some embodiments, the adipose tissue mimicking segment has an electron density ($n_e$) of 3.17E+23-3.20E+23 e–/g and an effective atomic number ($Z_{eff}$) of 6.3-6.4.

In some embodiments, the fibro-glandular tissue mimicking segment has an electron density ($n_e$) of 3.15E+23-3.45E+23 e–/g and an effective atomic number ($Z_{eff}$) of 6.9-7.4.

In some embodiments, the pectoral muscle mimicking segment has an electron density ($n_e$) of 3.40E+23-3.5E+23 e–/g and an effective atomic number ($Z_{eff}$) of 8.1-8.3.

In some embodiments, the carcinoma mimicking segment has an electron density ($n_e$) of 3.25E+23-3.65E+23 e–/g and an effective atomic number ($Z_{eff}$) of 7.1-7.5.

In some embodiments, the heterogeneous breast implant simulates the breast tissue under a medical imaging technique.

In some embodiments, the medical imaging technique is magnetic resonance imaging (MRI), computed tomography scan (CT scan), or both.

In yet another embodiment, a method of producing the heterogeneous breast phantom is provided wherein the method comprises casting a first composition that comprises polyvinyl alcohol and sugar to a skin-shaped mold, thereby forming the skin mimicking segment; casting a second composition that comprises beeswax to an adipose tissue-shaped mold, thereby forming the adipose tissue mimicking segment; casting a third composition that comprises glycerol to a fibro-glandular tissue-shaped mold, thereby forming the fibro-glandular tissue mimicking segment; casting a fourth composition that comprises sugar and optionally comprises egg whites to a pectoral muscle-shaped mold, thereby forming the pectoral muscle mimicking segment; casting a fifth composition that comprises sugar to a carcinoma-shaped mold, thereby forming the carcinoma mimicking segment; and, arranging the segments to produce the heterogeneous breast phantom such that the phantom represents a breast tissue.

In some embodiments, the method of producing the heterogeneous breast phantom is provided wherein at least one of the molds is produced via 3-dimensional (3D) printing.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

(FIG. 3A) outer skin, (FIG. 3B) skin, (FIG. 3C) fibro-glandular and (FIG. 3D) carcinoma mold.

DETAILED DESCRIPTION

Figure 1A:
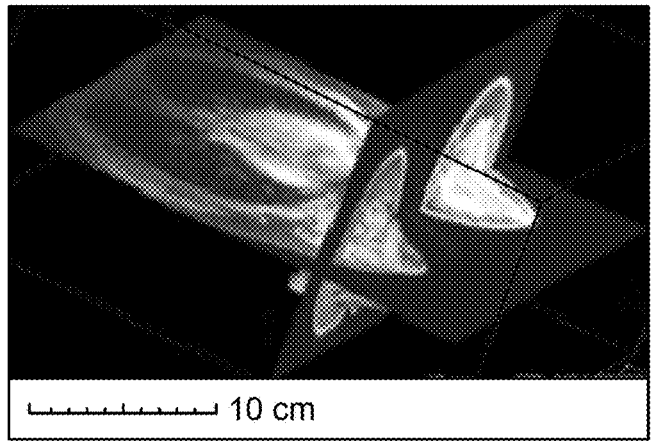
FIGS. 1A-1D are 3-dimensional (3D) segmented models comparable to the MRI image slices from different perspectives.
Figure 1B:
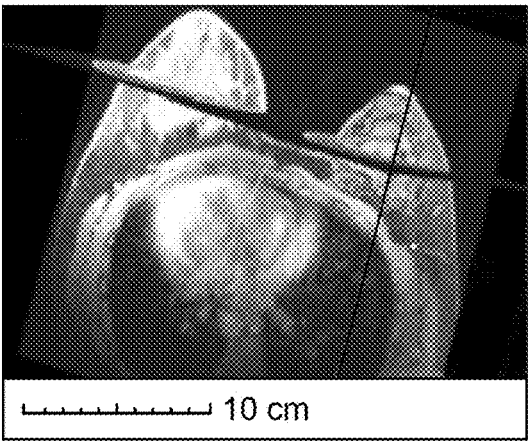
Figure 1C:
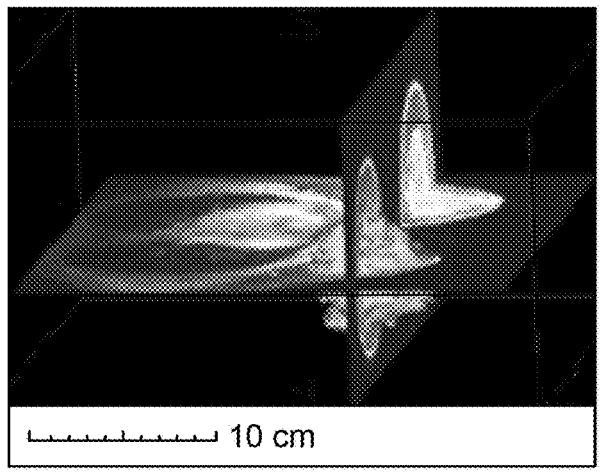
Figure 1D:
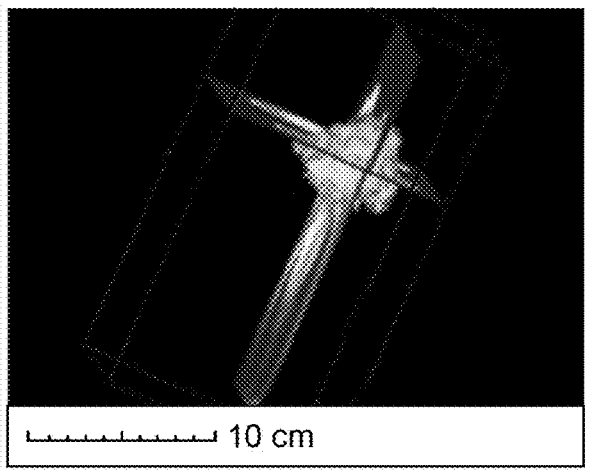

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

The existing medical imaging phantoms have a lot of limitations including unrealistic uniform background structure that does not mimic real organs and tissues. They are mostly designed with homogeneous (of the same properties everywhere in the phantom) solutions for the whole aimed organ with no accurate simulation of tumors, masses or other lesions. Additionally, most of the breast phantoms are tailored to function with a single imaging modality by simulating the tissue material response only for this single modality considering Quality Assurance (QA) only.

The present invention provides a single heterogeneous breast phantom (of different materials mimicking tissues and hence properties) that can be applicable to various imaging modalities with mimicking several breast tissues and carcinoma that can help in optimizing breast emerging systems and assessing the optimal radiation that would be subjected to the patient as well as QA purposes. In some embodiments, the inventive phantom offer advances in being patient-based developed, which can overcome the existing limitations in term of unrealistic structure.

In some embodiments, the invention is a heterogeneous anthropomorphic patient-based multi-modality breast phantom that mimics the real breast tissues in terms of anatomy and tissue properties concerning the conventional breast imaging techniques. The structured tissues of the phantom concern the skin, fibro-glandular tissue, adipose tissue, pectoral muscle and carcinoma with new developed tissue mimicking materials (TMMs). The purpose of the TMMs was to match the response of the real breast tissues when applied to ionizing and non-ionizing imaging modalities. The designed phantom revealed excellent ionizing radiation properties as the real breast tissues. These properties were the effective atomic number (Zeff), electron density (ne) and mass attenuation coefficient (MAC).

Moreover, the T1 and T2 relaxation times of the TMMs exhibited excellent agreement with the real breast tissues when examined at magnetic resonance imaging (MRI) laboratory at 0.5 Tesla. The fabricated breast phantom was tested using computed tomography (CT) and MRI machines, and the scanned images were in excellent agreement with the real tissues when examined using these machines. Two carcinoma TMMs of 2-cm. diameters were inserted in the breast, and they appeared clearly in the CT scanned images. The two carcinoma TMMs were modeled as malignant water content tissues and they appeared dark when T1-Weighted image contrast technique was used in MRI and bright when T2-Weighted image contrast technique was used.

The achieved results were in great agreement with the real water content carcinoma tissues when examined with an MRI using T1W and T2W.

The present invention provides a heterogeneous breast phantom comprising a skin mimicking segment that comprises polyvinyl alcohol and sugar; an adipose tissue mimicking segment that comprises beeswax; a fibro-glandular tissue mimicking segment that comprises glycerol; and a pectoral muscle mimicking segment that comprises sugar and optionally comprises egg whites, wherein each segment is shaped and arranged such that the breast phantom represents a breast tissue.

In some embodiments, each segment further comprises water, a vegetable oil, a surfactant, and agar.

The skin mimicking segment may comprise polymers, including natural polymers and synthetic polymers, which mimic the skin of a real breast. Exemplary natural polymers include, without limitation, agarose (i.e., agar), methylcellulose, and hyaluronan. Exemplary synthetic polymers include, without limitation, polyvinylpyrrolidone, polyvinyl alcohol, silicone (e.g., dimethicone, methicone, phenyl trimethicone, and cyclomethicone), polyacrylamide, polymacon, polyethylene oxide, poly(2-acrylamido-2-methyl-1-propanesulfonic acid), sodium polyacrylate, poly(hydroxyethyl methacrylate), polymethacrylate, polyethylacrylate, polyethylene terephthalate, polymethyl methacrylate, and copolymers thereof.

In preferred embodiments, the skin mimicking segment comprises polyvinyl alcohol and agar. The polyvinyl alcohol employed in the skin mimicking segment may have a weight average molecular weight from 20 kDa to 100 kDa, 40 kDa to 80 kDa, or 50 kDa to 75 kDa.

Exemplary sugars that may present in the skin mimicking segment include, but are not limited to, lactose, sucrose, mannitol, and sorbitol.

In some embodiments, polyvinyl alcohol and sugar are present in the skin mimicking segment in amounts of 4-6 wt. % and 27-35 wt. %, each relative to a total weight of the skin mimicking segment.

In some aspects of the invention, polyvinyl alcohol and sugar are present in the skin mimicking segment in amounts of 4, 4.5, 5.0, 5.5, or 6 wt. % and 27, 28, 29, 30, 31, 32, 33, 34 or 35 wt. %, each relative to a total weight of the skin mimicking segment. Preferably, polyvinyl alcohol is present in an amount of 5-5.5 wt % relative to a total weight of the skin mimicking segment. Preferably, sugar is present in an amount of 30-32 wt % relative to a total weight of the skin mimicking segment.

The skin mimicking segment may further comprise water, a surfactant (e.g., X-100 surfactant), an antimicrobial agent (e.g., quaternary ammonium salts such as benzalkonium chloride), and scattering particles.

The water used herein may be tap water, distilled water, bidistilled water, deionized water, deionized distilled water, reverse osmosis water, and/or some other water. Most preferably the water is deionized water.

Surfactants that may be present in the segments of the presently disclosed breast phantom include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., Triton™ X (e.g., Triton™ X-100), IGEPAL CA-630, Conco NI, Dowfax 9N, Igepal CO, Makon, Neutronyx 600's, Nonipol NO, Plytergent B, Renex 600's, Solar NO, Sterox, Serfonic N, T-DET-N, Tergitol NP, Triton N, sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof. In preferred embodiments, the surfactant is a nonionic surfactant. In a most preferred embodiment, the nonionic surfactant is Triton™ X-100.

Preferably, the surfactant present in the skin mimicking segment is a non-ionic surfactant such as Triton™ X-100.

Antimicrobial agents that may be present in the segments of the currently claimed breast phantom include quaternary ammonium salts such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, undecylenic acid, fluconazole, amphotericin B, sphingosine, and nystatin, triclosan, chlorhexidine, cetyl pyridinium chloride, benzethonium chloride, and bromochlorophene.

Preferably, the antimicrobial agent present in the skin mimicking segment is benzalkonium chloride.

The segments of the currently claimed breast phantom may further comprise at least one type of scattering particles selected from the group consisting of NaCl, KCl, $Al_2O_3$, and SiC particles. Preferably, the scattering particles present in the skin mimicking segment are NaCl particles.

The adipose tissue mimicking segment may comprise a wax, preferably beeswax, that mimics the adipose tissue of a real breast. In some embodiments, beeswax is present in the adipose tissue mimicking segment in an amount of 38-45 wt. % relative to a total weight of the adipose tissue mimicking segment.

In certain aspects of the invention, beeswax is present in the adipose tissue mimicking segment in an amount of 38, 39, 40, 41, 42, 43, 44 or 45 wt. % relative to a total weight of the adipose tissue mimicking segment. Preferably, beeswax is present in an amount of 42-43 wt % relative to a total weight of the adipose tissue mimicking segment.

In some embodiments, other waxes including carnauba wax, jojoba wax, and synthetic waxes may be used in addition to or in lieu of beeswax. In some embodiments, the waxes may have melting point in a range of 60 to 85° C. In certain examples, the waxes may have a melting point in a range of 62 to 82° C., 62 to 72° C., or 62 to 65° C.

The adipose tissue mimicking segment may further comprise water, agar, a surfactant, and scattering particles as defined above, and a vegetable oil. Preferably, the scattering particles present in the adipose mimicking segment are a mixture of NaCl, SiC, and KCl particles.

In some embodiments, vegetable oil, preferably safflower oil, may be present in segments of the breast phantom. In some embodiments, other vegetable oils such as olive oil, palm oil, rapeseed oil, soybean oil, corn oil, sunflower oil, cottonseed oil, peanut oil, grape seed oil, coconut oil, canola oil, or sesame oil may be used in lieu of or in addition to the safflower oil. Preferably, the vegetable oil present in the adipose tissue mimicking segment is safflower oil.

The fibro-glandular tissue mimicking segment may comprise a glycol, such as ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, and sorbitol. Preferably, the fibro-glandular tissue comprises glycerol. In some embodiments, glycerol is present in the fibro-glandular tissue mimicking segment in an amount of 10-15 wt. % relative to a total weight of the fibro-glandular tissue mimicking segment.

In certain aspects, glycerol is present in the fibro-glandular tissue mimicking segment in an amount of 10, 11, 12, 13, 14 or 15 wt. % relative to a total weight of the fibro-glandular tissue mimicking segment. Preferably, glycerol is present in an amount of 12-13 wt % relative to a total weight of the fibro-glandular tissue mimicking segment.

The fibro-glandular tissue mimicking segment may further comprise water, agar, a surfactant, an antimicrobial agent, scattering particles, and a vegetable oil as defined above. Preferably, the scattering particles present in the fibro-glandular mimicking segment are a mixture of SiC, $Al_2O_3$, and KCl particles.

In some embodiments, sugar is present in the pectoral muscle mimicking segment in an amount of 22-28 wt. % relative to a total weight of the pectoral muscle mimicking segment, and wherein egg whites, if present, are present in an amount of 2-8 wt. % relative to a total weight of the pectoral muscle mimicking segment.

In certain aspects, sugar is present in the pectoral muscle mimicking segment in an amount of 22, 21, 22, 23, 24, 25, 26, 27 or 28 wt. % relative to a total weight of the pectoral muscle mimicking segment, and wherein egg whites, if present, are present in an amount of 2, 3, 4, 5, 6, 7 or 8 wt. % relative to a total weight of the pectoral muscle mimicking segment. Preferably, sugar is present in an amount of 25-27 wt % relative to a total weight of the pectoral muscle mimicking segment. Preferably, egg whites are present in an amount of 3-4 wt % relative to a total weight of the pectoral muscle mimicking segment.

The pectoral muscle tissue mimicking segment may further comprise water, agar, a surfactant, an antimicrobial agent, and a vegetable oil as defined above.

In some embodiments, the heterogeneous breast phantom further comprises a carcinoma mimicking segment that comprises sugar.

In some embodiments, sugar is present in the carcinoma mimicking segment in an amount of 20-25 wt. % relative to a total weight of the carcinoma mimicking segment.

In some embodiments, sugar is present in the carcinoma mimicking segment in an amount of 20, 21, 22, 23, 24 or 25 wt. % relative to a total weight of the carcinoma mimicking segment. Preferably, sugar is present in an amount of 22-23 wt % relative to a total weight of the carcinoma mimicking segment.

The carcinoma mimicking segment may further comprise water, agar, an antimicrobial agent, and scattering particles as defined above. Preferably, the scattering particles present in the carcinoma mimicking segment are a mixture of NaCl and KCl particles.

Exemplary compositions of the skin mimicking segment, the adipose tissue mimicking segment, the fibro-glandular tissue mimicking segment, and the carcinoma mimicking segment according to this invention are given in Tables 1 through 5.

TABLE 1

Formula for the Skin

| Component | Component Weight (g) |
|---|---|
| Sodium Chloride (NaCl) | 15 |
| Deionized Water | 620 |
| Triton X-100 Surfactant | 30 |
| Polyvinyl alcohol (PVA) | 50 |
| Agar | 5 |
| Benzalkonium Chloride | 4 |
| Sugar | 300 |

TABLE 2

Formula for Adipose Tissue

| Component | Component Weight (g) |
|---|---|
| Sodium Chloride (NaCl) | 2 |
| Deionized Water | 110 |
| Triton X-100 Surfactant | 100 |
| Safflower oil | 315 |
| Beeswax | 400 |
| Agar | 7 |
| Silicon Carbide (SiC) | 4.9 |
| Potassium Chloride (KCl) | 6.5 |

TABLE 3

Formula for Fibro-glandular Tissue

| Component | Component Weight (g) |
|---|---|
| Silicone Carbide | 4 |
| Deionized Water | 663.8 |
| Triton X-100 Surfactant | 40 |
| Safflower Oil | 170 |
| Glycerol | 130 |
| Agar | 27 |
| Aluminum oxide | 15 |
| Potassium Chloride (KCl) | 5 |
| Benzalkonium Chloride | 5 |

TABLE 4

Formula for Carcinoma

| Component | Component Weight (g) |
|---|---|
| Sodium Chloride (NaCl) | 7 |
| Agar | 35 |
| Sugar | 220 |
| Deionized water | 700 |
| Benzalkonium Chloride | 3.5 |
| Potassium Chloride (KCl) | 1.9 |

TABLE 5

Formula for Pectoral Muscles

| Component | Component Weight (g) |
| --- | --- |
| Agar | 20 |
| Sugar | 360 |
| Deionized water | 900 |
| Benzalkonium Chloride | 4.14 |
| Triton X-100 Surfactant | 20 |
| Egg whites | 50 |
| Safflower oil | 40 |

The exemplary components for the TMMs in Tables 1-5 were based on choosing specific materials that have been modified and validated using the ionizing characteristic parameters as disclosed in Ruvio et al., "Multimodal Breast Phantoms for Microwave, Ultrasound, Mammography, Magnetic Resonance and Computed Tomography Imaging," Sensors, vol. 20, no. 8, Art. no. 8, January 2020; Quan et al., "Characterization of a dielectric phantom for high-field magnetic resonance imaging applications," Med. Phys., vol. 41, no. 10, October 2014; Oglat et al., "Chemical Items Used for Preparing Tissue-Mimicking Material of Wall-Less Flow Phantom for Doppler Ultrasound Imaging," J. Med. Ultrasound, vol. 26, no. 3, pp. 123-127, 2018; Lafon et al., An innovative synthetic tissue-mimicking material for high-intensity focused ultrasound. The Journal of the Acoustical Society of America, 2001, 110 (5), pp. 2613-2613; Manickam et al., "Development of a training phantom for compression breast elastography-comparison of various elastography systems and numerical simulations," J. Med. Imaging, vol. 2, no. 4, October 2015; Miyakawa et al., "Development of nonuniform breast phantom and its microwave imaging for tumor detection by CP-MCT," 2009 Annual International Conference of the IEEE Engineering in Medicine and Biology Society, Minneapolis, MN, USA, 2009, pp. 2723-2726; and Browne et al., "Tissue Mimicking Materials," 20200170612, 4 Jun. 2020 the entire disclosures of foregoing are incorporated herein by reference.

The structured tissues of the exemplary phantom concern the skin, fibro-glandular tissue, adipose tissue, pectoral muscle and carcinoma with new developed tissue mimicking materials (TMMs). The purpose of the TMMs was to match the response of the real breast tissues when applied to ionizing and non-ionizing imaging modalities.

The tissue-mimicking materials were characterized for modalities utilize ionizing radiation such as computed tomography and mammography. The TMMs of the exemplary phantoms were characterized analytically by using three important parameters which were mass attenuation coefficient, electron density ($n_e$) and effective atomic number ($Z_{eff}$). Mass attenuation coefficient describes how simply it can be penetrated by a beam of light, sound, particles, or other energy or matter as described in Hubell et al., "X-Ray Mass Attenuation Coefficients," NIST, https_://www.nist.gov/pml/x-ray-mass-attenuation-coefficients the entire disclosure is incorporated herein by reference. While the electron density measures the electron probability of existing in a unit volume of an element as disclosed in Khan et al., Khan's the physics of radiation therapy, Fifth edition. Philadelphia, PA: Lippincott Williams & Wilkins/Wolters Kluwer, 2014., the entire disclosure is incorporated herein by reference. $Z_{eff}$ is an element atomic number in which photons interact similar to a given composite material. It was found numerically by using National Institute of Standards and Technology (NIST) XCOM. The energies were specified according to the range used in each imaging modality after having the weight fractions for each tissue compounds.

From the mass density ($\rho m$) and atomic composition (z/A), the electron density of a material can be calculated according to the formula:

$$n_e = \rho_m \cdot N_A \cdot (z/A) \quad (1)$$

$$\text{where: } z/A = \Sigma_i a_i (z_i/A_i) \quad (2)$$

$N_A$ is Avogadro's number and $a_i$ is the fraction by weight of the ith element of atomic number $Z_i$ and atomic weight $A_i$ ranging from 0 to 8 depending on the elemental composition.

$Z_{eff}$ can be obtained from:

$$Z_{eff} = (\Sigma_{all\ tissue\ components(n)} a_n Z_n^{2.94})^{1/2.94} \quad (3)$$

Where $a_n$ represent the fractional contribution of each element to the total number of electrons in mixture.

Based on the International Commission on Radiation Units (ICRU), reference values elemental composition weight fractions of the real tissues were compared and validated with the above calculations.

The weight fractions of the exemplary TMMs elements were calculated for each breast tissue of skin, fibro-glandular, adipose, pectoral muscle, and malignant carcinoma. Table 6 presents the resulted weight fractions of TMMs comparable to the real breast tissue elemental compositions weight fractions found from ICRU reports. The values were close to the real especially when focusing on the main tissue elements which are C, H and O for all tissues.

Table 7 was developed based on Equations (1) and (2) which present the specific tissue electron density and effective atomic number. Low errors were observed with maximum of 5.76% for fibro-glandular $Z_{eff}$ and minimum of 0.00415% for pectoral muscle $n_e$. That means the exemplary materials and quantities can produce similar real breast tissue interactions when exposed to ionizing radiations with energies in the range 10-150 KeV.

In some embodiments, the skin mimicking segment has an electron density ($n_e$) of 3.59E+23-3.61E+23 e−/g, preferably about 3.60 E+23 e−/g, and an effective atomic number ($Z_{eff}$) of 7.2-7.3, preferably about 7.22.

In some embodiments, the adipose tissue mimicking segment has an electron density ($n_e$) of 3.17E+23-3.20E+23 e−/g, preferably about 3.20 E+23 e−/g, and an effective atomic number ($Z_{eff}$) of 6.3-6.4, preferably about 6.33.

In some embodiments, the fibro-glandular tissue mimicking segment has an electron density ($n_e$) of 3.15E+23-3.45E+23 e−/g, preferably about 3.18 E+23 e−/g, and an effective atomic number ($Z_{eff}$) of 6.9-7.4, preferably about 6.93.

In some embodiments, the pectoral muscle mimicking segment has an electron density ($n_e$) of 3.40E+23-3.5E+23 e−/g, preferably about 3.44 E+23 e−/g, and an effective atomic number ($Z_{eff}$) of 8.1-8.3, preferably about 8.18.

In some embodiments, the carcinoma mimicking segment has an electron density ($n_e$) of 3.25E+23-3.65E+23 e−/g, preferably about 3.57 E+23 e−/g and an effective atomic number ($Z_{eff}$) of 7.1-7.5, preferably about 7.11.

FIGS. 4, 5, 6, 7 and 8 show the mass attenuation coefficient against the applied photonic energy for the exemplary skin, adipose tissue, fibro-glandular tissue, malignant carcinoma, and pectoral muscles tissues, respectively for both real ICRU elemental compositions and the phantom calculated elemental compositions. All the introduced tissue-mimicking materials of the exemplary phantom revealed a good agreement in all the energy range of energy with insignificant differences in the range of small applied photonic energy. The mass attenuation coefficient for the skin and adipose tissue real and calculated results showed a great overlapped graph for all points with high similarity.

In some embodiments, the heterogeneous breast implant simulates the breast tissue under a medical imaging technique, such as computed tomography (CT), magnetic resonance imaging (MRI), ultrasonography, and X-ray imaging.

In preferred embodiments, the medical imaging technique is magnetic resonance imaging (MRI), computed tomography scan (CT scan), or both.

The exemplary phantom revealed excellent ionizing radiation properties as the real breast tissues. These properties were the effective atomic number ($Z_{eff}$), electron density ($n_e$) and mass attenuation coefficient (MAC). Moreover, the T1 and T2 relaxation times of the TMMs exhibited excellent agreement with the real breast tissues when examined at a magnetic resonance imaging (MRI) laboratory at 0.5 Tesla. The fabricated breast phantom was tested using computed tomography (CT) and MRI machines, and the scanned images were in excellent agreement with the real tissues when examined using these machines. The TMMs of the present disclosure provide the same breast tissues ionizing radiation properties (reflection coefficient, electron density, and effective atomic number) when exposed to X-rays in CT, Radiographic and Mammographic imaging modalities.

Figure 10:
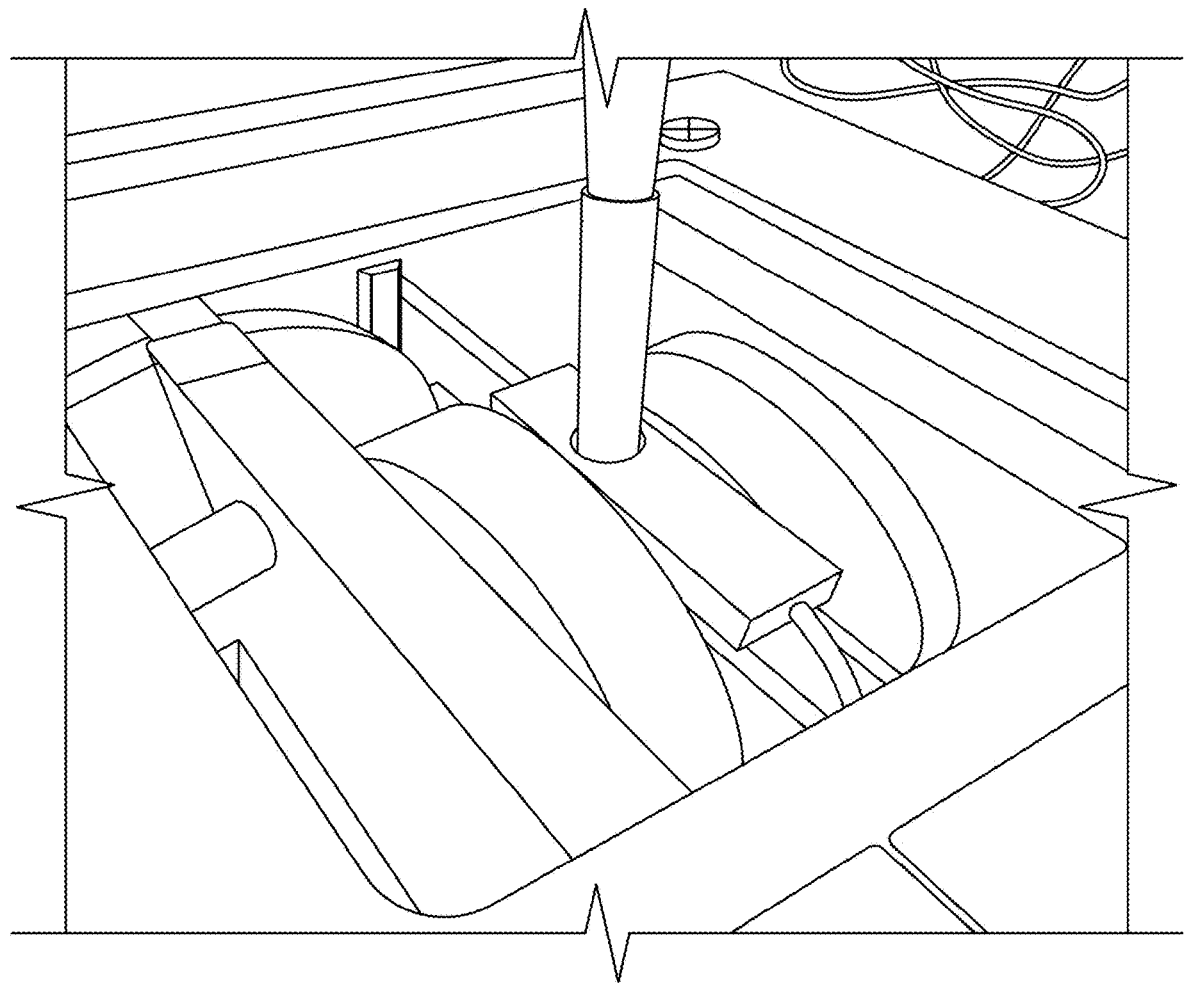
FIG. 10 shows measurement of T1 and T2 relaxation times of the TMMs.

Two exemplary carcinoma TMMs of 2-cm. diameter were inserted in the breast, and they appeared clearly in the CT scanned images. The two carcinoma TMMs were modeled as malignant water content tissues and thus they appeared dark when T1-Weighed image contrast technique is used in MRI and bright when T2-Weighted image contrast technique is used. The achieved results were in great agreement with the real water content carcinoma tissues when examined with MRI using T1W and T2W, as shown in Table 8. Measurements of T1 and T2 relaxation times of exemplary TMMs are shown in FIG. 10.

TABLE 7

Skin, Fibro-glandular, Adipose, Pectoral Muscles and Carcinoma Electron Density and $Z_{eff}$.

| Tissue | | Electron density | Error % | $Z_{eff}$ | Error % |
|---|---|---|---|---|---|
| Skin | Phantom | 3.59776E+23 | 0.163 | 7.22 | 0.558 |
| | ICRU | 3.60362E+23 | | 7.2630298 | |
| Adipose | Phantom | 3.39E+23 | 0.0315 | 7.33E+00 | 5.76 |
| | ICRU | 3.17967E+23 | | 6.93E+00 | |
| Fibroglandular | Phantom | 3.19937E+23 | 0.619 | 6.391046106 | 0.956 |
| | ICRU | 3.17967E+23 | | 6.330516684 | |
| Pectoral Muscles | Phantom | 3.43E+23 | 0.00415 | 8.29E−01 | 0.195 |
| | ICRU | 3.44E+23 | | 8.184042E−1 | |
| Carcinoma | Phantom | 3.57E+23 | 2.93 | 7.46E+00 | 4.46 |
| | ICRU | 3.31E+23 | | 7.11E+00 | |

TABLE 8

Comparing real and measured (T1, T2) for adipose and pectoral muscle tissues.

| | T1 | | T2 | |
|---|---|---|---|---|
| Tissue | Real (0.5 T) | Measured (0.5 T) | Real (0.5 T) | Measured (0.5 T) |
| Adipose tissue | 0.102 s [49] | 0.131 s | 0.08 s [49] | 0.082 s |
| Pectoral muscle | 0.560 s [49] | 0.586 s | 0.034 s [49] | 0.053 s |

The TMMs of the present disclosure have substantially the same T1 and T2 relaxation times of real breast tissues when exposed to static magnetic fields of 0.5T and 1.5T and in the existence of a rotating field. The TMMs can therefore also be used effectively in MRI.

Additionally, the mass attenuation coefficients in cm2/g of the exemplary phantom tissues were found and plotted against the real breast tissues mass attenuation coefficients in

TABLE 6

| Breast Phantom Elemental Compositions Weight Fractions | | | | | | |
|---|---|---|---|---|---|---|
| Tissue | | Na | Cl | C | H | O |
| Skin | Phantom | 0.004821033 | 0.007692516 | 0.275323873 | 0.098487258 | 0.613573165 |
| | ICRU | 0.001 | 0.003 | 0.204 | 0.1 | 0.645 |
| Adipose | Phantom | 0.000832225 | 0.004552743 | 0.689825033 | 0.12133871 | 0.17621494 |
| | ICRU | 0.001 | 0.001 | 0.598 | 0.114 | 0.278 |
| Fibro-glandular | Phantom | — | 0.002619926 | 0.218820618 | 0.105858707 | 0.659929689 |
| | ICRU | 0.001 | 0.001 | 0.332 | 0.106 | 0.527 |
| Pectoral Muscles | Phantom | — | 0.000234935 | 0.16631 | 0.096804967 | 0.73072 |
| | ICRU | 0.0008 | — | 0.123 | 0.101997 | 0.720993 |
| Carcinoma | Phantom | 0.002849483 | 0.005615315 | 0.116584436 | 0.098753539 | 0.776084016 |
| | ICRU | — | — | 0.187626775 | 0.101419878 | 0.668356998 |

| Breast Phantom Elemental Compositions Weight Fractions | | | | | | | | |
|---|---|---|---|---|---|---|---|---|
| Tissue | | Mg | K | N | S | P | Si | Al |
| Skin | Phantom | — | — | 0.000102156 | — | — | — | — |
| | ICRU | — | 0.001 | 0.042 | 0.002 | 0.001 | — | — |
| Adipose | Phantom | — | 0.003605935 | — | — | — | 0.003630414 | — |
| | ICRU | — | — | 0.007 | 0.001 | — | — | — |
| Fibrogla-ndular | Phantom | — | 0.002477372 | 0.000147657 | — | — | 0.002646044 | 0.007499987 |
| | ICRU | — | — | 0.03 | 0.002 | 0.001 | — | — |
| Pectoral Muscles | Phantom | — | — | 0.005929387 | — | — | — | — |
| | ICRU | 0.002 | 0.0002 | 0.035 | 0.005 | 0.002 | — | — |
| Carcinoma | Phantom | — | 0.001031131 | 0.000113212 | — | — | — | — |
| | ICRU | — | — | 0.042596349 | — | — | — | — | the energy range of 10 KeV to 150 KeV, as clinically used in mammography and CT machines.

A particularly preferred embodiment of the invention includes reference points or target areas, e.g., gelled point, having different gelation characteristics than any of the adipose tissue mimicking, a fibro-glandular tissue mimicking and pectoral muscle mimicking segments. These gelled points can be formed by the inclusion of a gelling agent, preferably pectin, or a cross-linking agent such as an alkali metal salt during fabrication. Gelled points represent portions of the breast phantom in which the density of the material is different from its immediate surroundings. Gelled points can function as training aids or as a means of determining distance in the three-dimensional breast phantom structure. Gelled points preferably have a diameter dimension of 0.5-2.0 mm, preferably 1.0-1.5 mm. The dimension may be determined by x-ray, CT or MRI where the outer limit of gelling point represents a portion of the phantom composition having an absorption of at least 90% preferably 95% the value of the absorption of the phantom tissue measured at a portion of the breast phantom that is separate from the gelled point, for example separated from the center point of the gelled point by a distance of 5 mm, preferably 10 mm. In this respect the gelled points have a gradient characteristic with greatest density at the center point decreasing outwardly from the center point. Preferably the density of the gelled points is at least 5% greater than the density of the surrounding fence and tissue, preferably at least 7.5% or at least 9% greater. In another preferred embodiment, the breast phantom includes a plurality of gelled points equidistantly spaced within a plane of the breast phantom. For example, four gelled points may represent a bottom or horizontal plane through the breast phantom. A vertical plane that may share one or more gelled points with the horizontal plane but also includes at least four gelling points is also present. The vertical and horizontal planes are preferably perpendicular to one another although embodiments in which the planes are at an angle other than 90° are possible such as 45°, 60° or 85°. The gelled points typically represent less than 5% of the weight total weight of breast phantom, preferably less than 2%, less than 0.5% or less than 0.05% of the total weight of the breast phantom.

Figure 9:
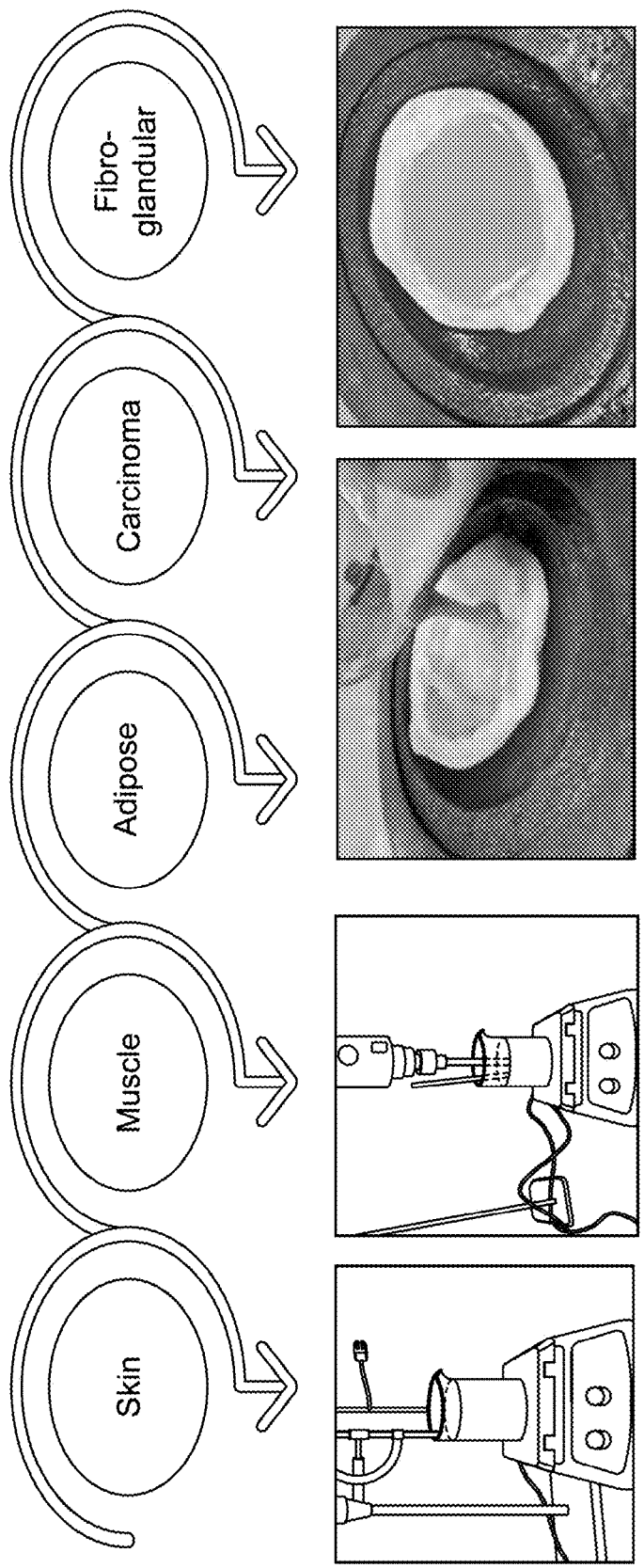
FIG. 9 shows fabrication methods for TMMs.
Figure 13:
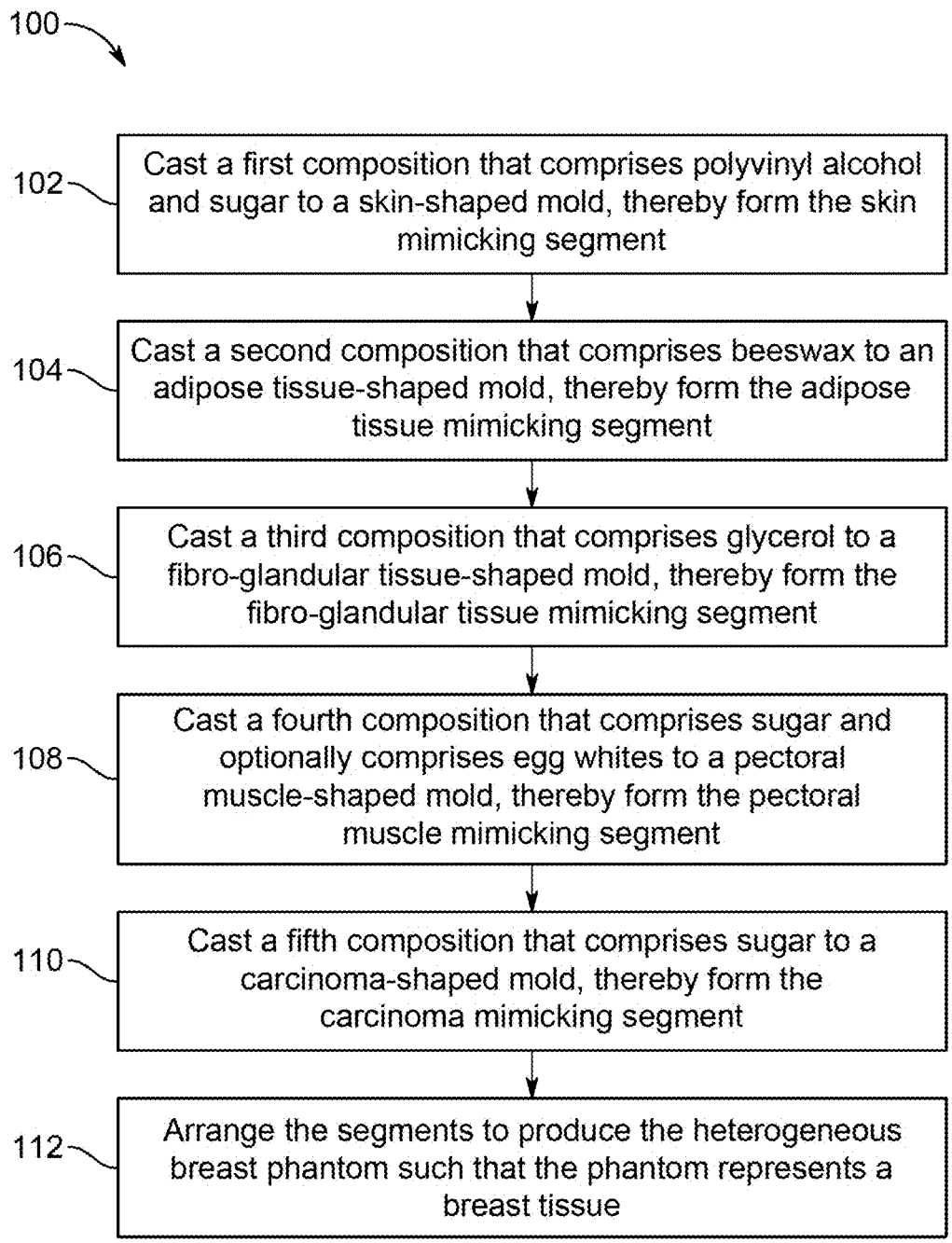
FIG. 13 is a schematic flow diagram of a method of producing the heterogeneous breast phantom.

In yet another embodiment, referring to FIG. 13, a method 100 of producing the heterogeneous breast phantom is provided wherein the method 100 comprises, at step 102, casting a first composition that comprises polyvinyl alcohol and sugar to a skin-shaped mold, thereby forming the skin mimicking segment; at step 104, casting a second composition that comprises beeswax to an adipose tissue-shaped mold, thereby forming the adipose tissue mimicking segment; at step 106, casting a third composition that comprises glycerol to a fibro-glandular tissue-shaped mold, thereby forming the fibro-glandular tissue mimicking segment; at step 108, casting a fourth composition that comprises sugar and optionally comprises egg whites to a pectoral muscle-shaped mold, thereby forming the pectoral muscle mimicking segment; at step 110, casting a fifth composition that comprises sugar to a carcinoma-shaped mold, thereby forming the carcinoma mimicking segment; and, at step 112, arranging the segments to produce the heterogeneous breast phantom such that the phantom represents a breast tissue. FIG. 9 shows exemplary methods for fabrication of TMMs.

Figure 11:
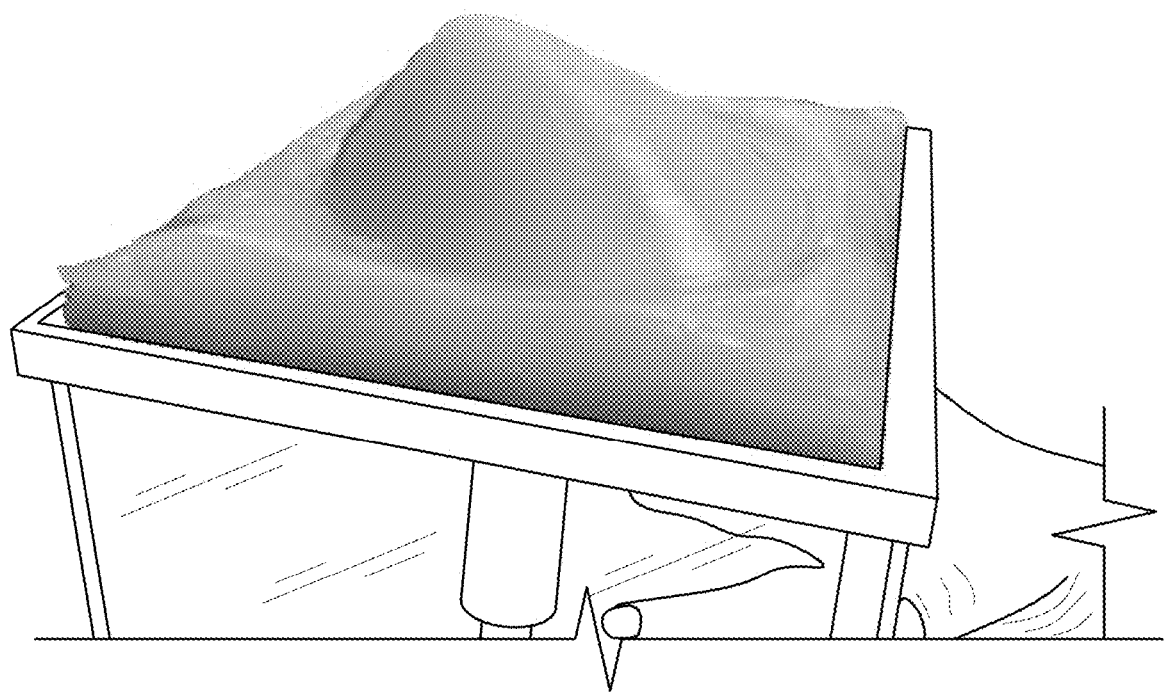
FIG. 11 shows the fabricated breast phantom.
Figure 12:
FIG. 12 shows validation of the phantom using clinical CT and breast MRI Machines.

In some embodiments, the method 100 of producing the heterogeneous breast phantom is provided wherein at least one of the molds is produced via 3D printing. Alternatively, the molds may be produced by processing techniques such as extrusion, co-extrusion, injection molding, blow molding, vacuum forming, thermos-forming, elasto-welding, pultrusion, compression molding, and other fabrication techniques. An exemplary fabricated breast phantom is shown in FIG. 11. The validation of an exemplary phantom using CT and breast MRI machines is shown in FIG. 12.

Materials and Methods

Definitions of Terms $n_e$=Electron Density
$Z_{eff}$=Effective atomic number

From the mass density ($\rho_m$) and atomic composition (z/A), the electron density of a material can be calculated according to the formula:

$$n_e = \rho_m \cdot N_A \cdot (z/A) \quad (1)$$

$$\text{where: } z/A = \Sigma_i a_i (z_i/A_i) \quad (2)$$

$N_A$ is Avogadro's number and $a_i$ is the fraction by weight of the $i^{th}$ element of atomic number $Z_i$ and atomic weight $A_i$ ranging from 0 to 8 depending on the elemental composition.

$Z_{eff}$ can be obtained from:

$$Z_{eff} = (\Sigma_{all\ tissue\ components(n)} a_n Z_n^{2.94})^{1/2.94} \quad (3)$$

where $a_n$ represent the fractional contribution of each element to the total number of electrons in mixture.

A. Patient Data Acquisition

Institutional Review Board (IRB) approval was obtained from King Fahd Specialist Hospital (KFSH) in Saudi Arabia, Dammam (RAD0319), in order to use patient data. A Digital Imaging and Communications in Medicine (DICOM) magnetic resonance imaging (MRI) breast image with dynamic contrast-enhancement is used. The criteria of patient data selection were built upon the BI-RADS which was established by American College of Radiology (ACR). The score of the chosen image was I (normal breast) with dense fibro-glandular tissues to be inserted with a malignant lesion.

B. Image Segmentation and Creation of Molds

For breast tissue segmentation, the acquired MR breast images were imported into segmentation software. This was to have a realistic separated geometry for the external shape, skin, fibro-glandular tissue and tumor. The patient DICOM images were imported into 3D slicer software with 128 slices for internal tissues segmentation to segment out the skin and fibro-glandular tissue from the surrounding adipose. The purpose was to ensure a complete elimination of all the surrounding structures. Each slice was segmented in different orientations to improve segmentation reliability using the threshold function, which was adjusted manually. Afterwards, the segmented fibro-glandular tissue was converted into 3D model and saved as Standard Triangle Language (STL) file for further processing. Negative and positive molds were created from the segmented skin layer to create a single flask for the skin and adipose tissue. Segmented fibro-glandular was modified to create a base for handling purposes. Segmented fibro-glandular was modified to create a base for handling purposes. Also, a tumor mold of 2 cm diameter was created. The molds of the external breast shape, skin, and fibro-glandular were printed using acrylonitrile butadiene styrene (ABS) plastic to have a high realistic distribution of the interior structure, specifically for the fibro-glandular mold as described in Burfeindt et al., "MRI-Derived 3-D-Printed Breast Phantom for Microwave Breast Imaging Validation," IEEE Antennas Wirel. Propag. Lett., vol. 11, pp. 1610-1613, 2012, the entire disclosure is incorporated herein by reference.

Image Segmentation

For the patient DICOM images segmentation to extract the region of interest (ROI) through detection of boundaries, breast outer shape and fibro-glandular tissue was separated from other surrounding tissues using 3D Slicer software to have a realistic separated geometry for the external shape, skin and fibro-glandular tissue. The resulted 3D fibro-glandular volume model comparable to the axial and coronal images slices with high anatomical precision shown in FIGS. 1A-1D from different perspectives. The segmented model presented a need for further smoothing and processing to be able for 3D printing without defects.

3D Mold Fabrication

Figure 2:
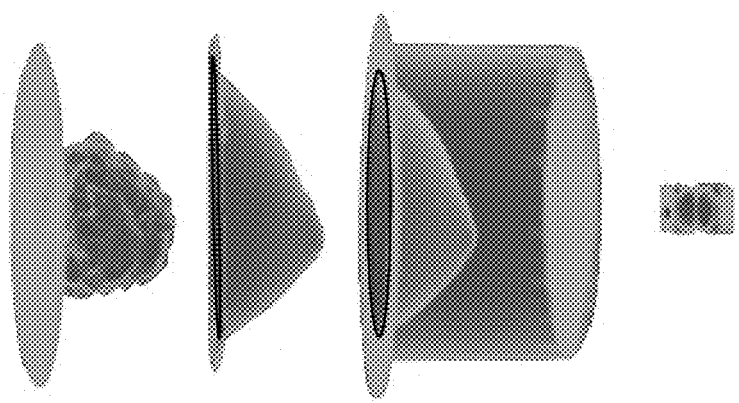
FIG. 2 is a 3D phantom molds design.
Figure 3A:
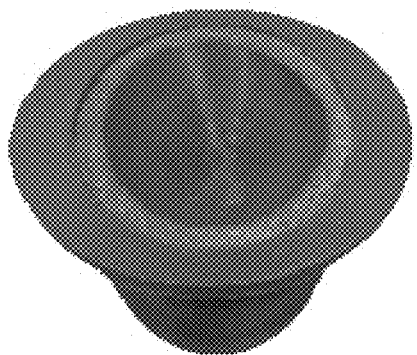
FIGS. 3A-3D show breast phantom molds.
Figure 3B:
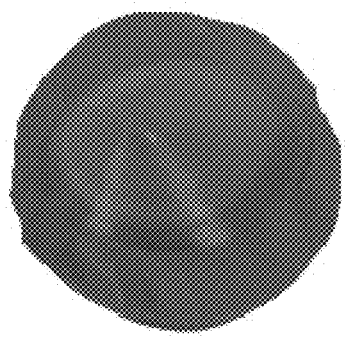
Figure 3C:
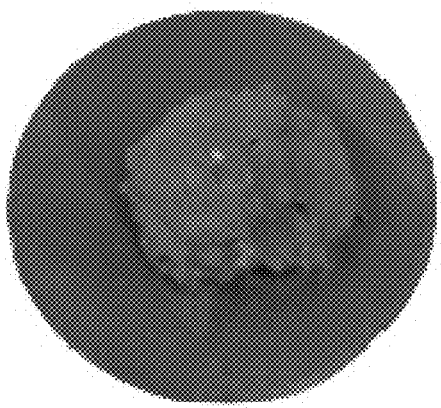
Figure 3D:
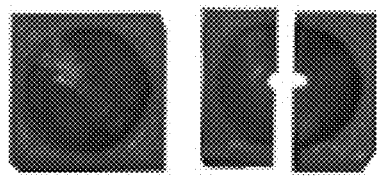
Figure 4:
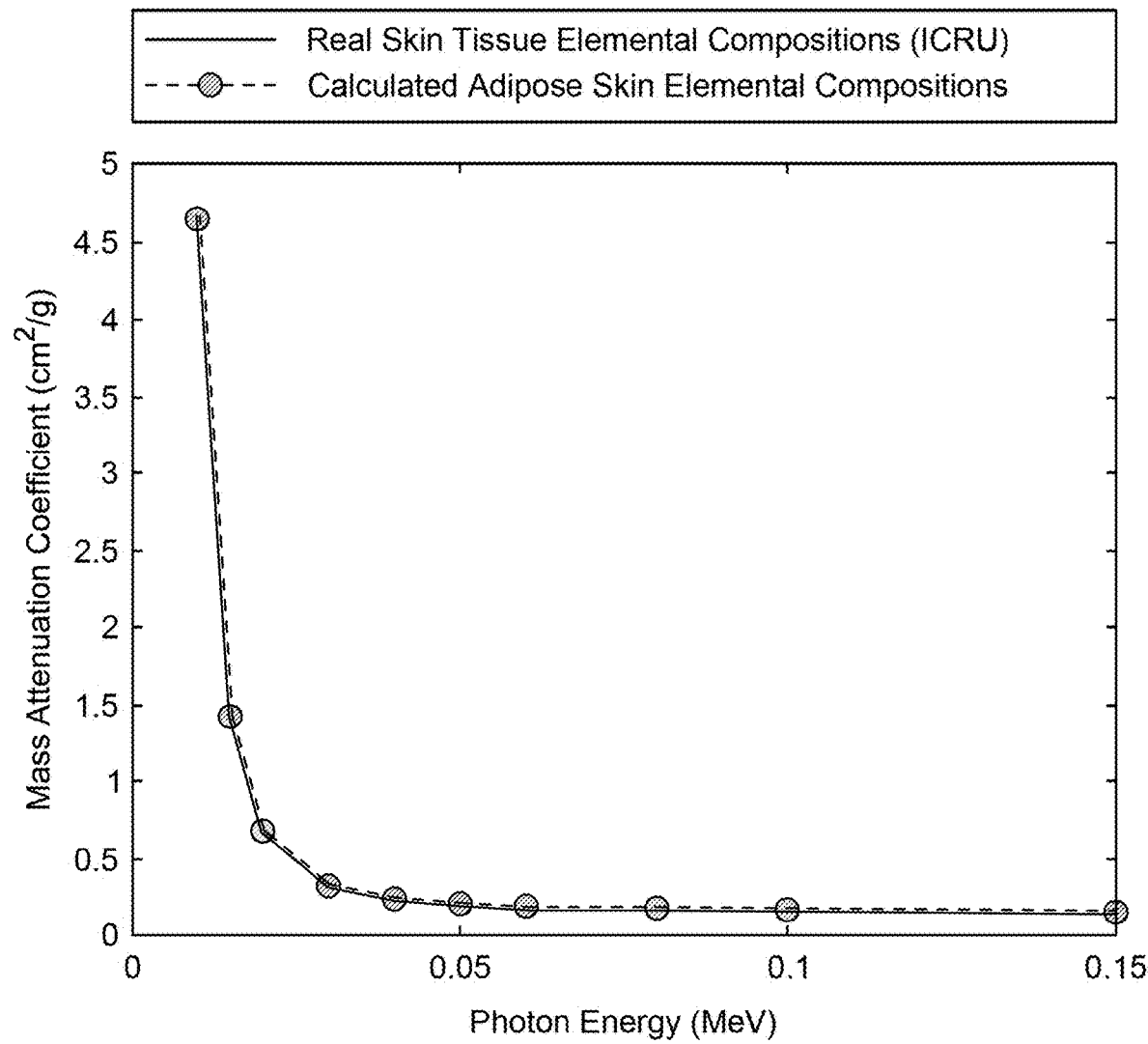
FIG. 4 shows real and calculated skin elemental compositions photon energy vs. mass attenuation coefficient graph.
Figure 5:
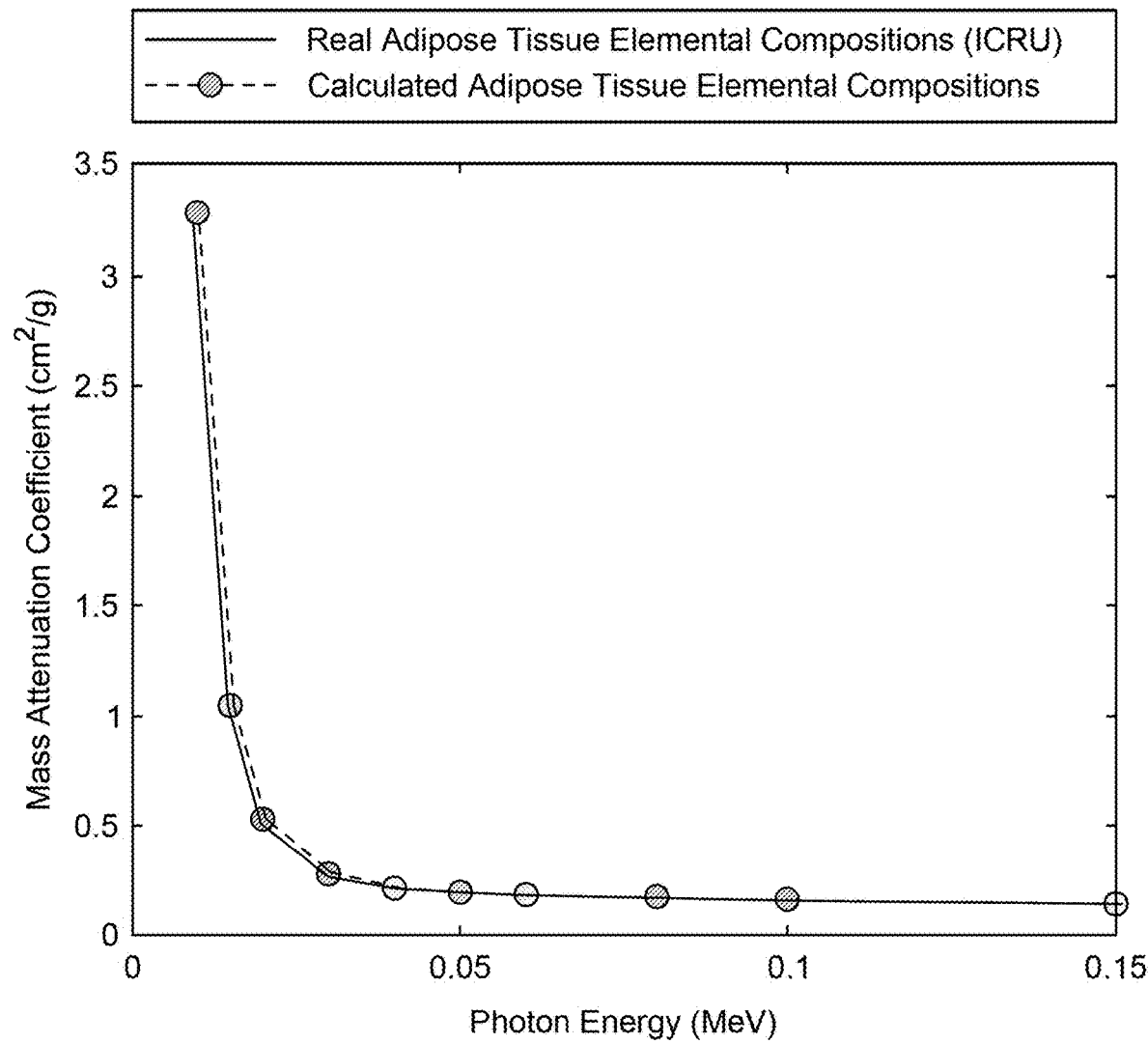
FIG. 5 shows real and calculated Adipose elemental compositions photon energy vs. mass attenuation coefficient graph.
Figure 6:
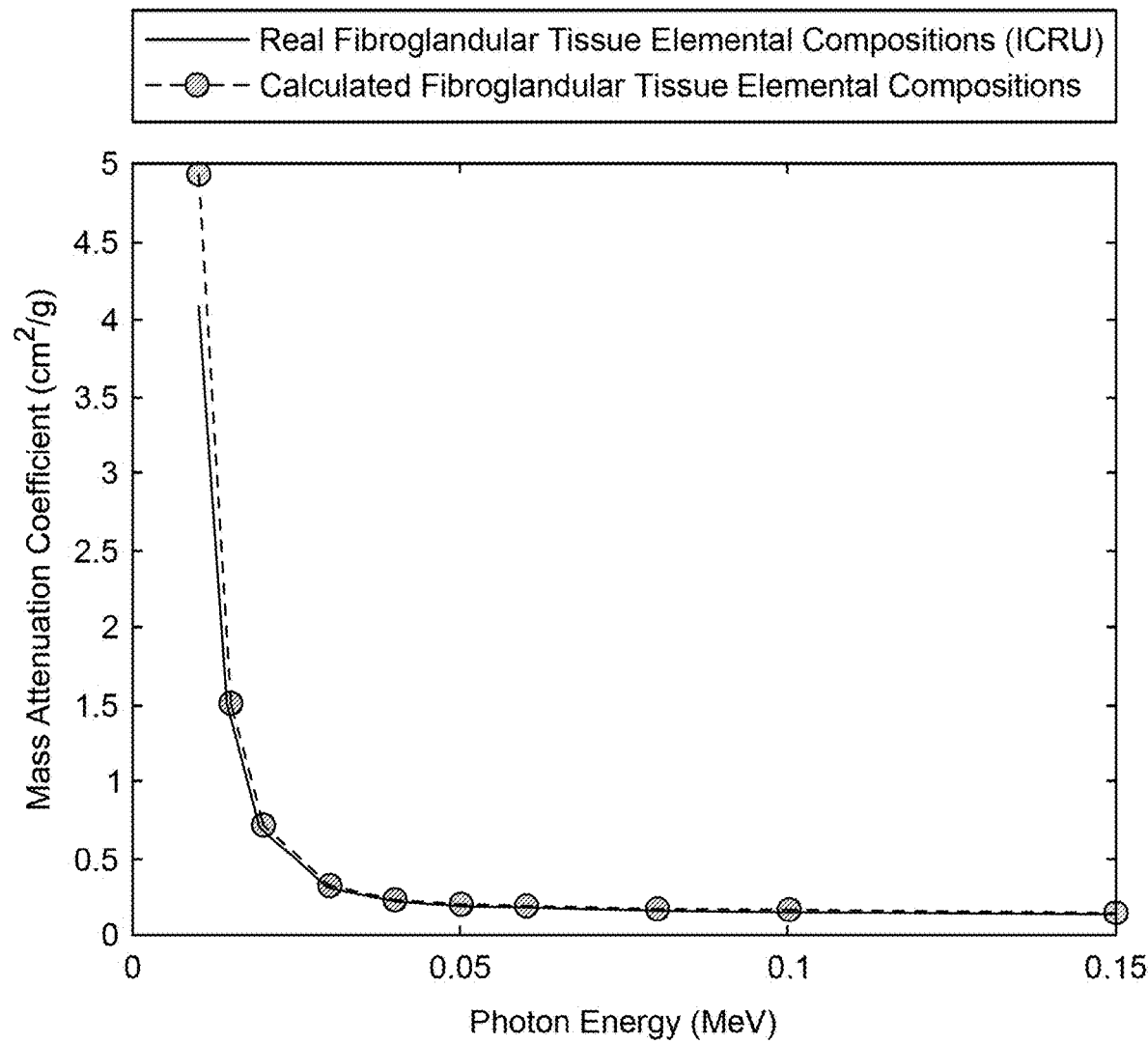
FIG. 6 shows real and calculated fibro-glandular elemental compositions photon energy vs. mass attenuation coefficient graph.
Figure 7:
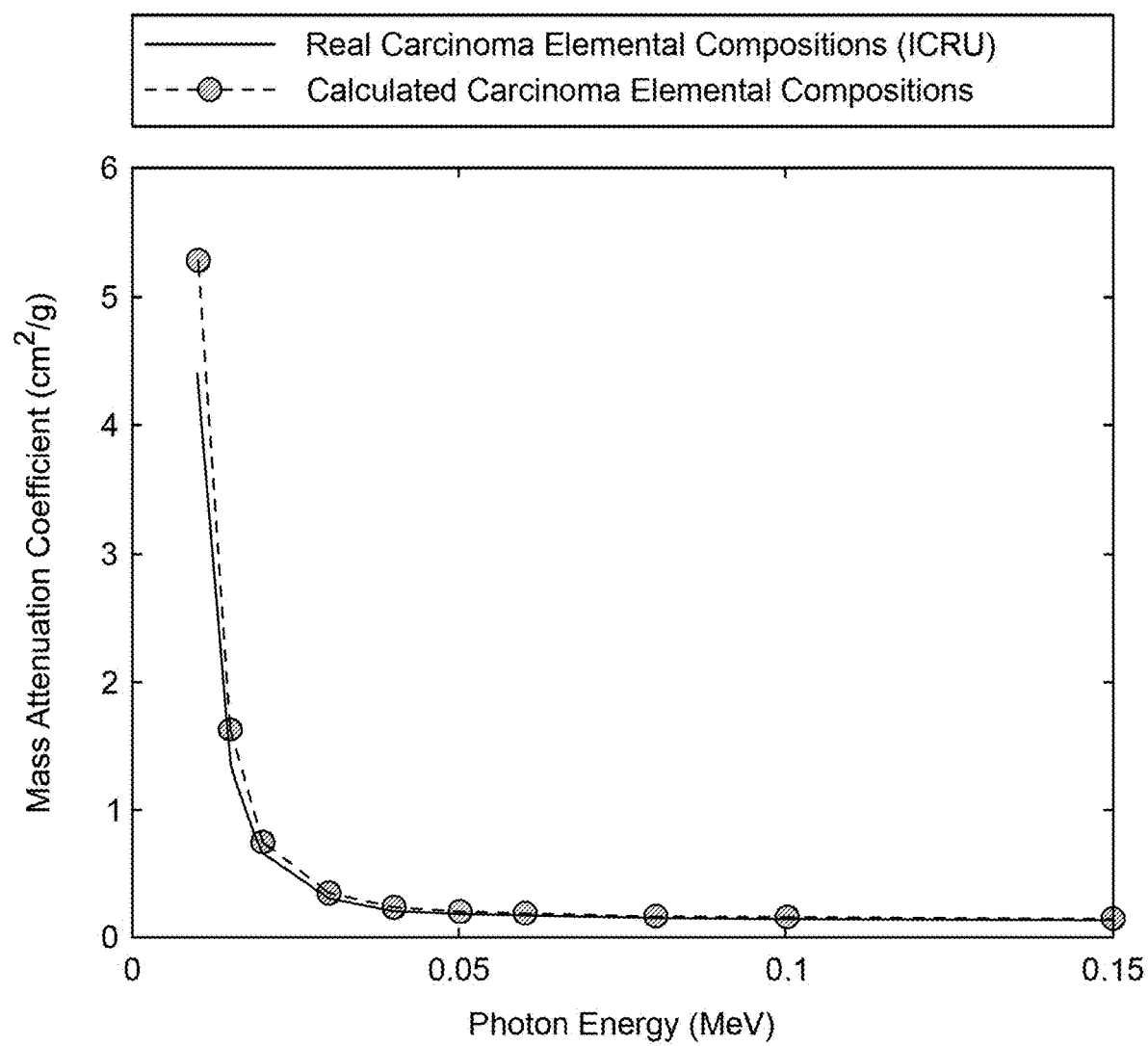
FIG. 7 shows real and calculated carcinoma elemental compositions photon energy vs. mass attenuation coefficient graph.
Figure 8:
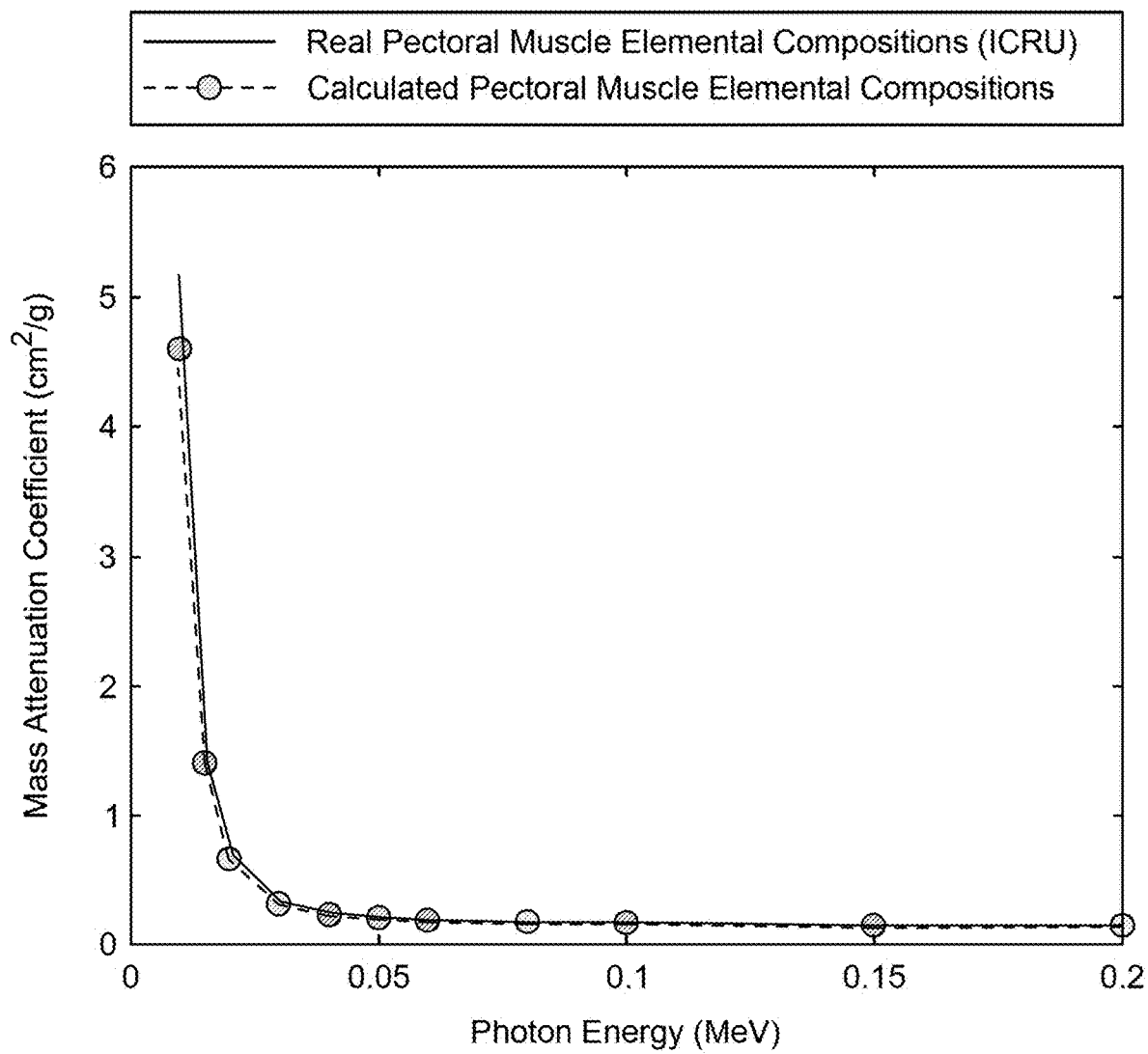
FIG. 8 shows real and calculated pectoral muscle elemental compositions photon energy vs. mass attenuation coefficient graph.

Free-floating and deformities were removed, and model hollows were edited during this process. The skin was converted into a negative mold to represent the outer shape of the phantom. In this outer shape mold, a 3 mm thickness was added at the rounded corners to create the skin tissue thickness. The fibro-glandular STL file was edited to have an applicable adipose to fibro-glandular interface surface for printing. FIG. 2 presents all processed molds.

The 3D models of the phantom were printed in Namthaja 3D printing manufacturing solutions, Saudi Arabia, Dammam. The printed external shape, skin, fibro-glandular, and tumor molds are shown in FIG. 3.

Numerous modifications and variations of the present invention are possible in light of the above teachings. It is therefore to be understood that within the scope of the appended claims, the invention may be practiced otherwise than as specifically described herein.

The invention claimed is:

1. A heterogeneous breast phantom, comprising:
  a skin mimicking segment that comprises polyvinyl alcohol and sugar, wherein the polyvinyl alcohol and the sugar are present in the skin mimicking segment in amounts of 4-6 wt % and 27-35 wt % respectively, each relative to a total weight of the skin mimicking segment;
  an adipose tissue mimicking segment that comprises beeswax and agar, wherein beeswax is present in the adipose tissue mimicking segment in an amount of 38-45 wt % relative to a total weight of the adipose tissue mimicking segment;
  a fibro-glandular tissue mimicking segment that comprises glycerol, wherein the glycerol is present in the fibro-glandular tissue mimicking segment in an amount of 10-15 wt % relative to a total weight of the fibro-glandular tissue mimicking segment;
  a pectoral muscle mimicking segment that comprises sugar and egg whites, wherein the sugar is present in the pectoral muscle mimicking segment in an amount of 22-28 wt %, and wherein the egg whites are present in an amount of 2-8 wt % relative to a total weight of the pectoral muscle mimicking segment, and
  a carcinoma mimicking segment that comprises a sugar selected from the group consisting of lactose, sucrose, mannitol, and sorbitol in an amount of 20-25 wt % relative to a total weight of the carcinoma mimicking segment;
  wherein each segment is shaped and arranged such that the breast phantom represents a breast tissue.

2. The heterogeneous breast phantom of claim 1, wherein each segment further comprises water, a vegetable oil, a surfactant, and agar.

3. The heterogeneous breast phantom of claim 2, wherein the vegetable oil is safflower oil.

4. The heterogeneous breast phantom of claim 2, wherein the surfactant is a nonionic surfactant.

5. The heterogeneous breast phantom of claim 1, wherein the skin mimicking segment, the adipose tissue mimicking segment, the fibro-glandular tissue mimicking segment, and the carcinoma mimicking segment each further comprise at least one type of scattering particles selected from the group consisting of NaCl, KCl, $Al_2O_3$, and SiC particles.

6. The heterogeneous breast phantom of claim 1, wherein the skin mimicking segment has an electron density ($n_e$) of 3.59E+23-3.61E+23 $e^-$/g and an effective atomic number ($Z_{eff}$) of 7.2-7.3
  wherein the adipose tissue mimicking segment has an electron density ($n_e$) of 3.17E+23-3.20E+23 $e^-$/g and an effective atomic number ($Z_{eff}$) of 6.3-6.4,
  wherein the fibro-glandular tissue mimicking segment has an electron density ($n_e$) of 3.15E+23-3.45E+23 $e^-$/g and an effective atomic number ($Z_{eff}$) of 6.9-7.4, and
  wherein the pectoral muscle mimicking segment has an electron density ($n_e$) of 3.40E+23-3.5E+23 $e^-$/g and an effective atomic number ($Z_{eff}$) of 8.1-8.3.

7. The heterogeneous breast phantom of claim 1, which simulates the breast tissue under a medical imaging technique.

8. The heterogeneous breast phantom of claim 7, wherein the medical imaging technique is magnetic resonance imaging (MRI), computed tomography scan (CT scan), or both.

* * * * *